(12) United States Patent
Chen et al.

(10) Patent No.: US 7,354,467 B2
(45) Date of Patent: Apr. 8, 2008

(54) FILTERING ASSEMBLY IN NASAL CAVITIES

(76) Inventors: Yung-Zhem Chen, No. 98, Wen Nan Rd., South District, Tainan City (TW); Shin-Hsiang Cheng, No. 15. Lane 20, Bei Cheng Rd., North District, Tainan City (TW)

( * ) Notice: Subject to any disclaimer, the term of this patent is extended or adjusted under 35 U.S.C. 154(b) by 163 days.

(21) Appl. No.: 11/356,987

(22) Filed: Feb. 21, 2006

(65) Prior Publication Data

US 2007/0193233 A1    Aug. 23, 2007

(51) Int. Cl.
*B01D 46/00* (2006.01)
*A61M 15/08* (2006.01)

(52) U.S. Cl. ............... 55/385.1; 128/204.12; 128/206.11; 128/207.18

(58) Field of Classification Search ............... 55/385.1, 55/DIG. 35; 128/204.11, 204.12, 206.11, 128/207.18
See application file for complete search history.

(56) References Cited

U.S. PATENT DOCUMENTS

| | | | | |
|---|---|---|---|---|
| 701,538 A * | 6/1902 | Carence | ............... | 128/204.12 |
| 2,151,227 A * | 3/1939 | Pawelek | ............... | 128/206.11 |
| 2,277,390 A * | 3/1942 | Crespo | ............... | 128/204.12 |
| 2,433,565 A * | 12/1947 | Korman | ............... | 128/204.12 |
| 2,777,442 A * | 1/1957 | Zelano | ............... | 128/206.11 |
| 3,457,917 A * | 7/1969 | Mercurio | ............... | 128/204.12 |
| 3,463,149 A * | 8/1969 | Albu | ............... | 128/204.12 |
| 3,722,509 A * | 3/1973 | Nebel | ............... | 128/204.12 |
| 3,905,335 A * | 9/1975 | Kapp | ............... | 128/206.11 |
| 4,030,491 A * | 6/1977 | Mattila | ............... | 128/206.11 |
| 4,267,831 A * | 5/1981 | Aguilar | ............... | 128/203.14 |
| 4,327,719 A * | 5/1982 | Childers | ............... | 128/206.11 |
| 5,417,205 A * | 5/1995 | Wang | ............... | 128/206.11 |
| 5,425,359 A * | 6/1995 | Liou | ............... | 128/206.11 |
| 5,890,491 A * | 4/1999 | Rimkus | ............... | 128/206.11 |
| 6,962,156 B2 * | 11/2005 | Michaels | ............... | 128/206.11 |
| 6,971,387 B2 * | 12/2005 | Michaels | ............... | 128/206.11 |
| 6,971,388 B1 * | 12/2005 | Michaels | ............... | 128/206.11 |
| 7,156,098 B2 * | 1/2007 | Dolezal et al. | ........ | 128/206.11 |
| 7,156,099 B1 * | 1/2007 | Jenkins | ............... | 128/206.11 |
| 2003/0209145 A1 * | 11/2003 | Soper | ............... | 95/273 |
| 2004/0065065 A1 * | 4/2004 | Van Patten | ............... | 55/385.1 |
| 2004/0261798 A1 * | 12/2004 | Rimkus | ............... | 128/206.11 |
| 2005/0051170 A1 * | 3/2005 | Koo | ............... | 128/206.11 |
| 2006/0016450 A1 * | 1/2006 | Pearson et al. | ........ | 128/206.11 |
| 2007/0175478 A1 * | 8/2007 | Brunst | ............... | 128/206.18 |

* cited by examiner

*Primary Examiner*—Duane Smith
*Assistant Examiner*—Robert A Clemente (57) ABSTRACT

A filtering assembly in nasal cavities includes a connector with two rings connected by a link, and two filtering members are securely connected to the two rings. The two filtering members are inserted into the wearer's nasal cavities so as to effectively filter foreign objects from entering to the wearer's lungs.

4 Claims, 8 Drawing Sheets

FILTERING ASSEMBLY IN NASAL CAVITIES

FIELD OF THE INVENTION

The present invention relates to a filtering assembly including two filtering members connected to a connector and the filtering members are inserted into a user's nasal cavities.

BACKGROUND OF THE INVENTION

There are many people suffered by different kinds of pollution in this modern world and the pollutions cause several problems to our noses such as allergic rhinitis and sinusitis. The sources of pollution come from two main sources, one of which is from industry factories, such as carbon monoxide, cyanogens compound particles and heavy metal particles. The other main source is from transportation system, such as air-crafts, vehicles, motorcycles or ships. The pollutions are in forms of tiny particles spread in the air and enter into people's bodies from noses. Although there are nose hairs in our noses to filter foreign objects, the tiny particles are so many and so tiny that they cannot be effectively filtered just by the nose hairs in noses. In order to prevent the tiny particles of pollutions from entering our noses, some people wear masks which cover the nose and mouth. However, most of the masks are made by fabrics which includes orifices between fibers and these orifices are too big for the tiny particles so that the wearers still inhale these tiny particles via noses. Besides, the masks cannot perfectly match the contour of the wearers' face and gaps are formed between the face and the masks and these tiny particles are easily inhaled into the wearers' lungs.

The present invention intends to provide a filtering assembly which includes a connector with two rings and two filtering members are connected to the two rings. The filtering members can be inserted into the nasal cavities so as to effectively filter the foreign particles.

SUMMARY OF THE INVENTION

The present invention relates to a filtering assembly in nasal cavities and comprises a connector having two rings connected by a link, and two filtering members connected to the two rings. The two filtering members are inserted into the wearer's nasal cavities.

The primary object of the present invention is to provide a filtering assembly that can be directly inserted in the nasal cavities.

Another object of the present invention is to provide a filtering assembly that is easily to be manufactured at low cost.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Figure 1:
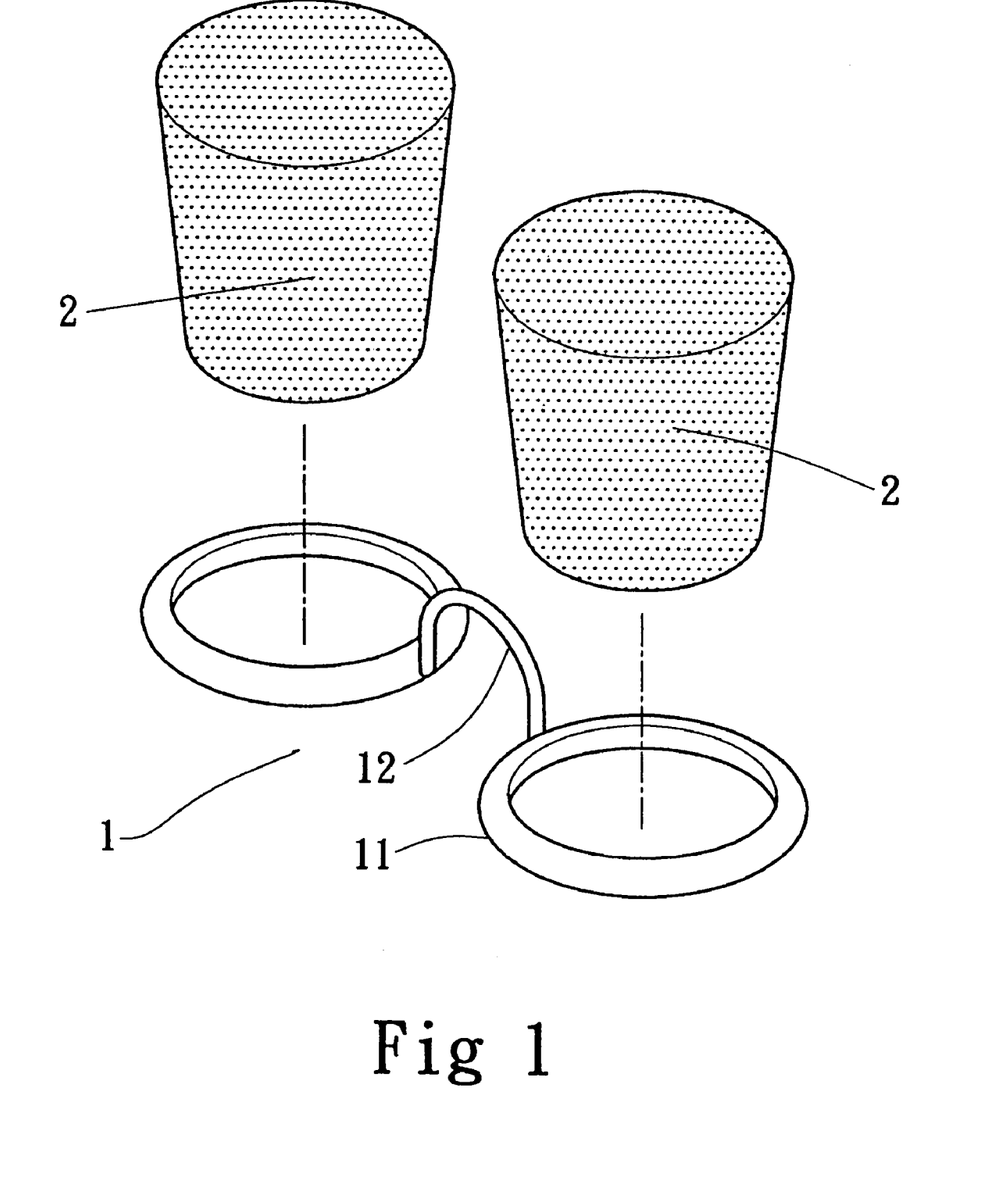
FIG. 1 is an exploded view to show the filtering assembly of the present invention.
Figure 2:
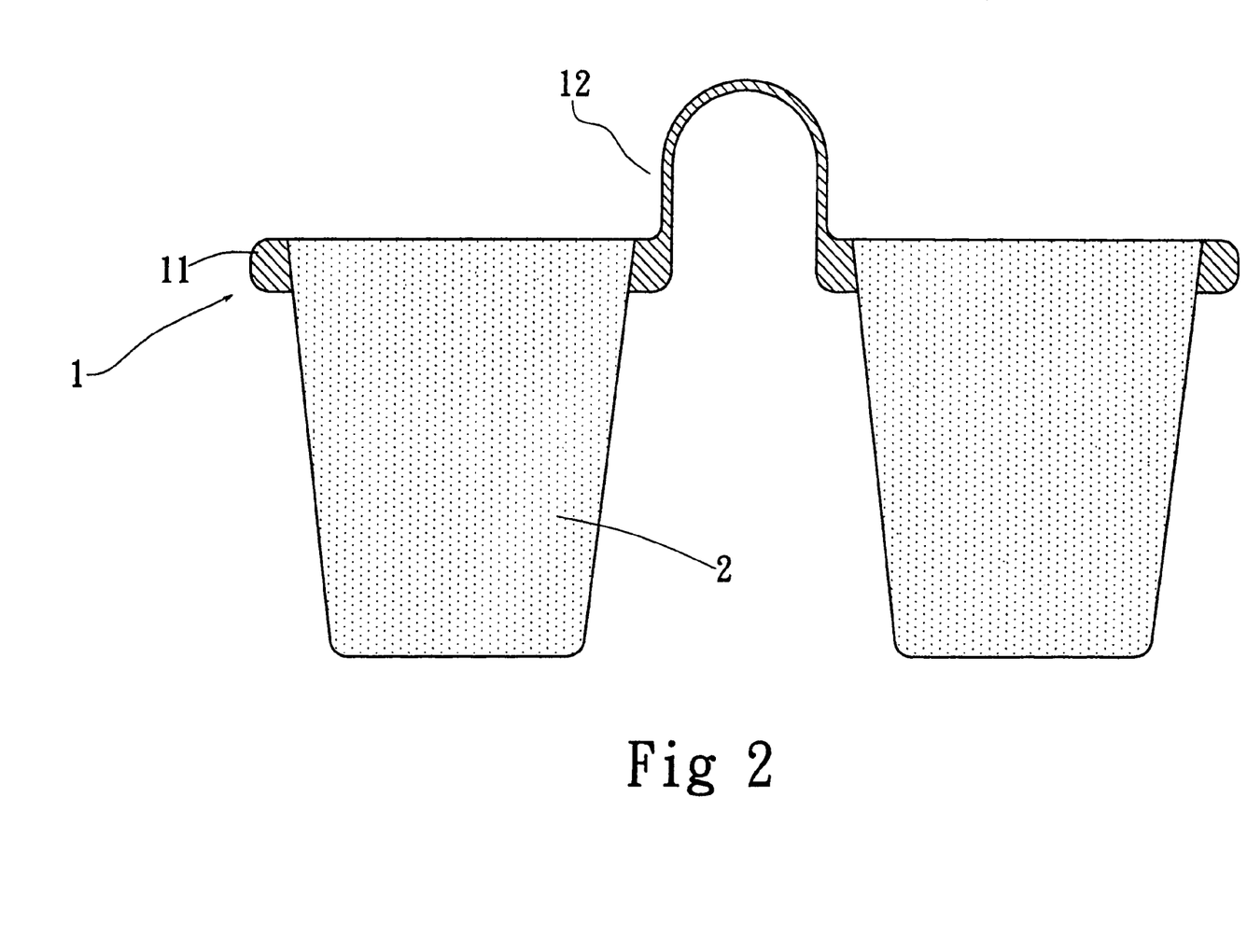
FIG. 2 is a cross sectional view to show the filtering assembly of the present invention.
Figure 3:
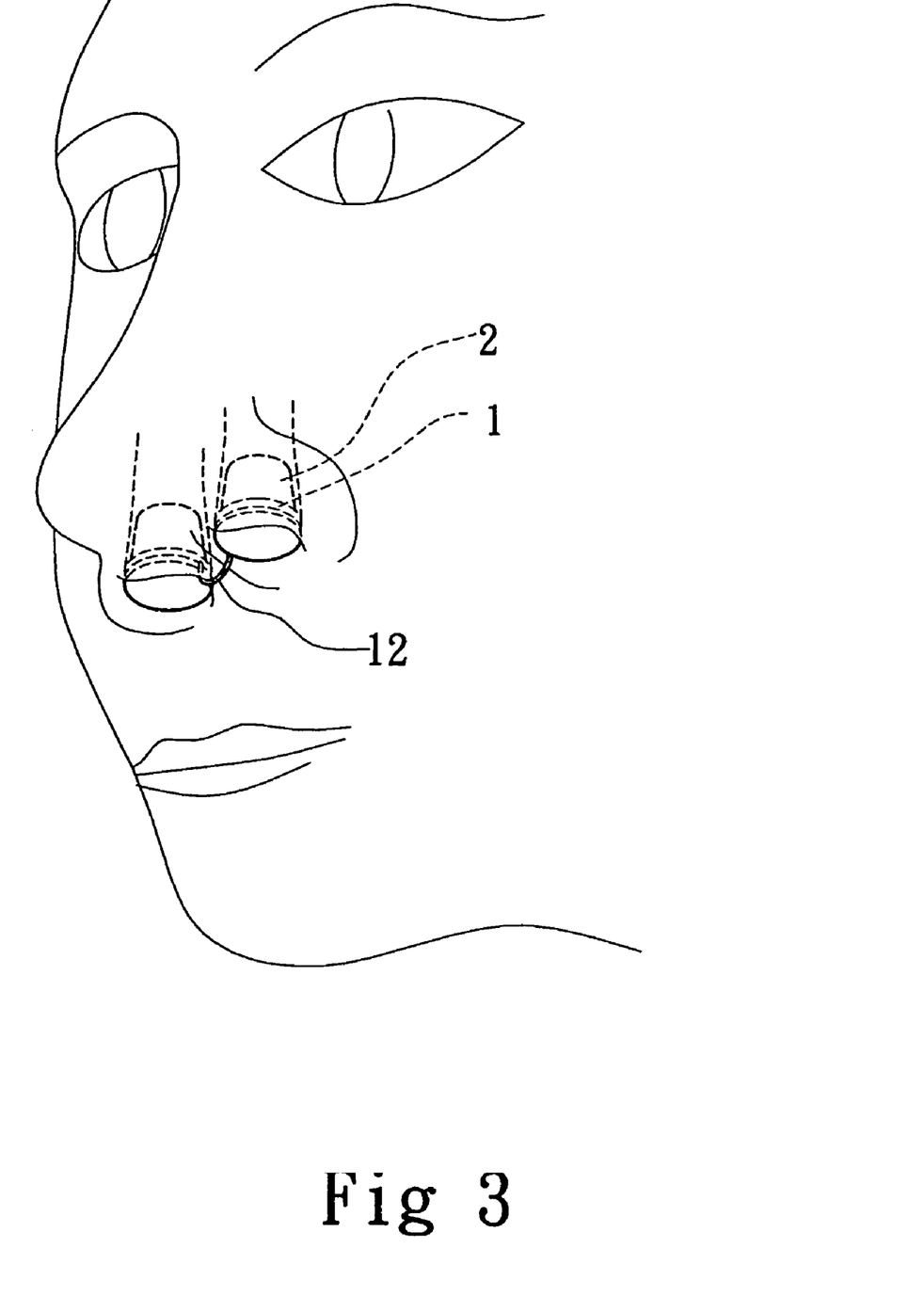
FIG. 3 shows the filtering members of the filtering assembly of the present invention are inserted into the wearer's nasal cavities.

Referring to FIGS. 1 to 3, the filtering assembly of the present invention comprises a connector 1 which includes two rings 11 connected by a link 12. The link 12 is a curved link and can be made by plastic material. Two filtering members 2 are securely connected to the two rings 11. The two filtering members 2 are directly inserted into the nasal cavities of the wearer to filter foreign objects such as the tiny particles of pollutions from entering into the wearer's lungs. The filtering members 2 are secured to the rings 11 by way of heat fusion, gluing or any known methods.

Figure 4:
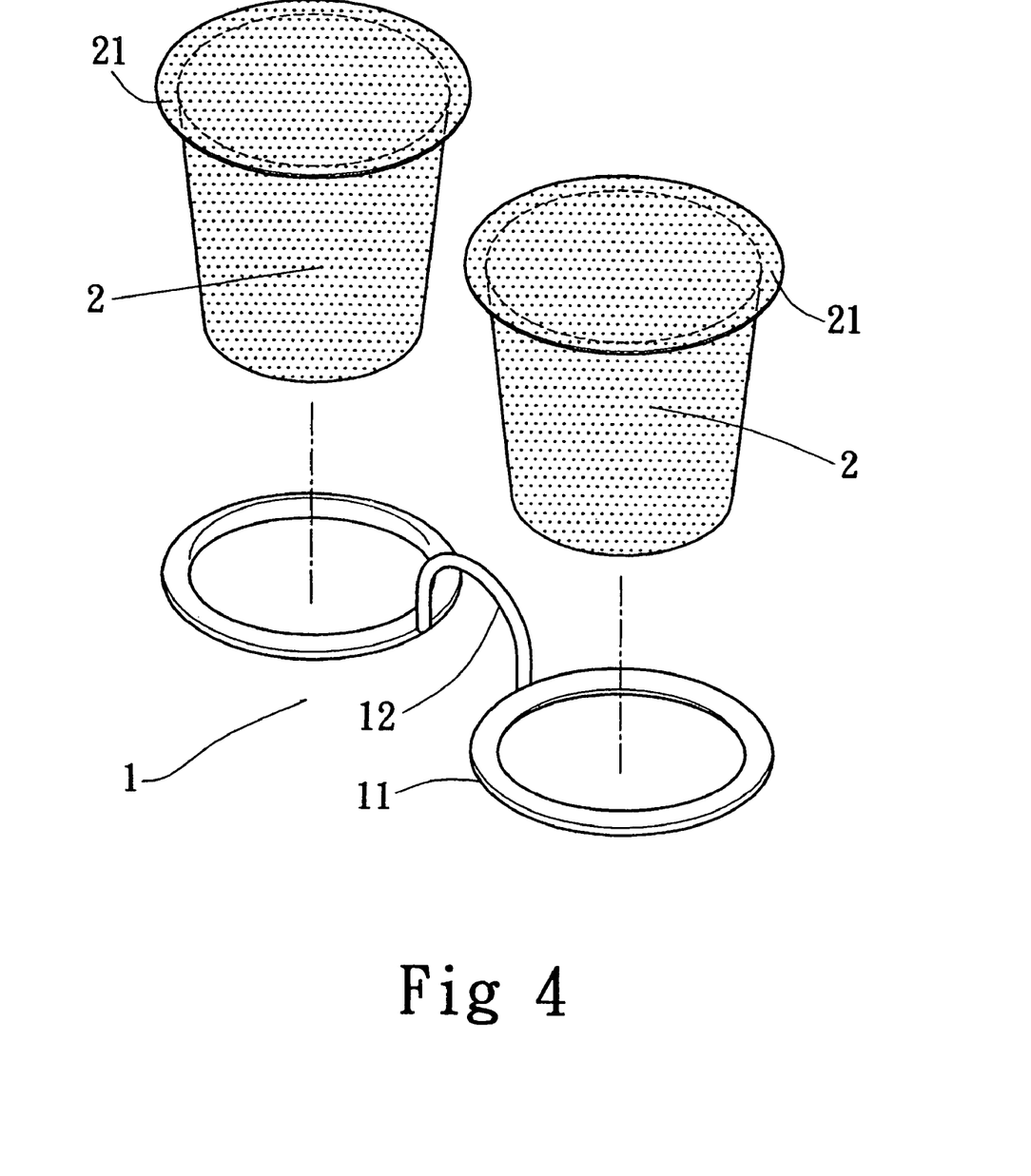
FIG. 4 shows another embodiment of the filtering members.
Figure 5:
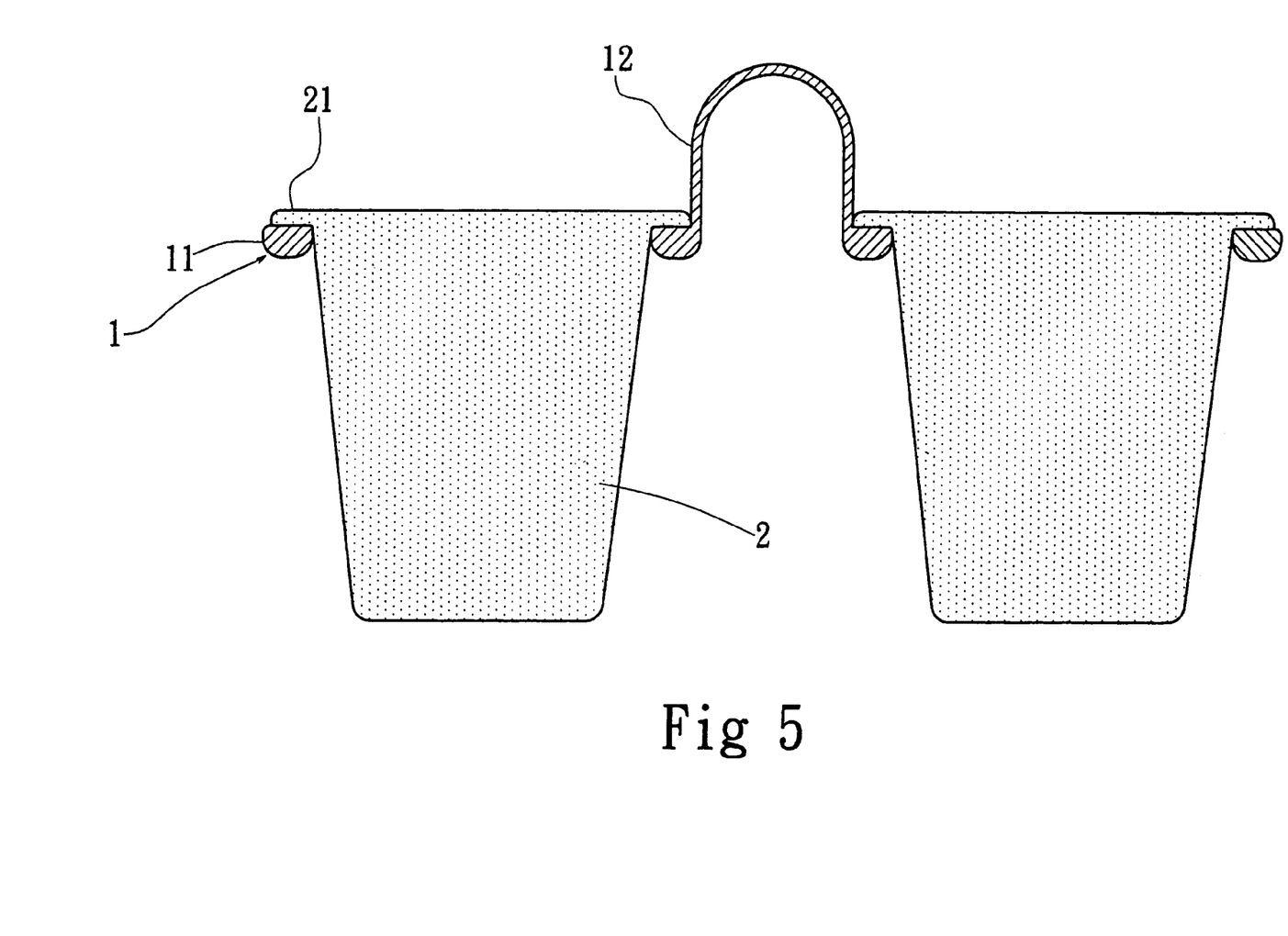
FIG. 5 is a cross sectional view to show the filtering assembly of the embodiment in FIG. 4.

FIGS. 4 and 5 show another embodiment of the filtering members 2 wherein the two filtering members 2 each have a flange 21 extending outward from an end thereof and the flanges 21 are secured to two respective top surfaces of the rings 11.

Figure 6:
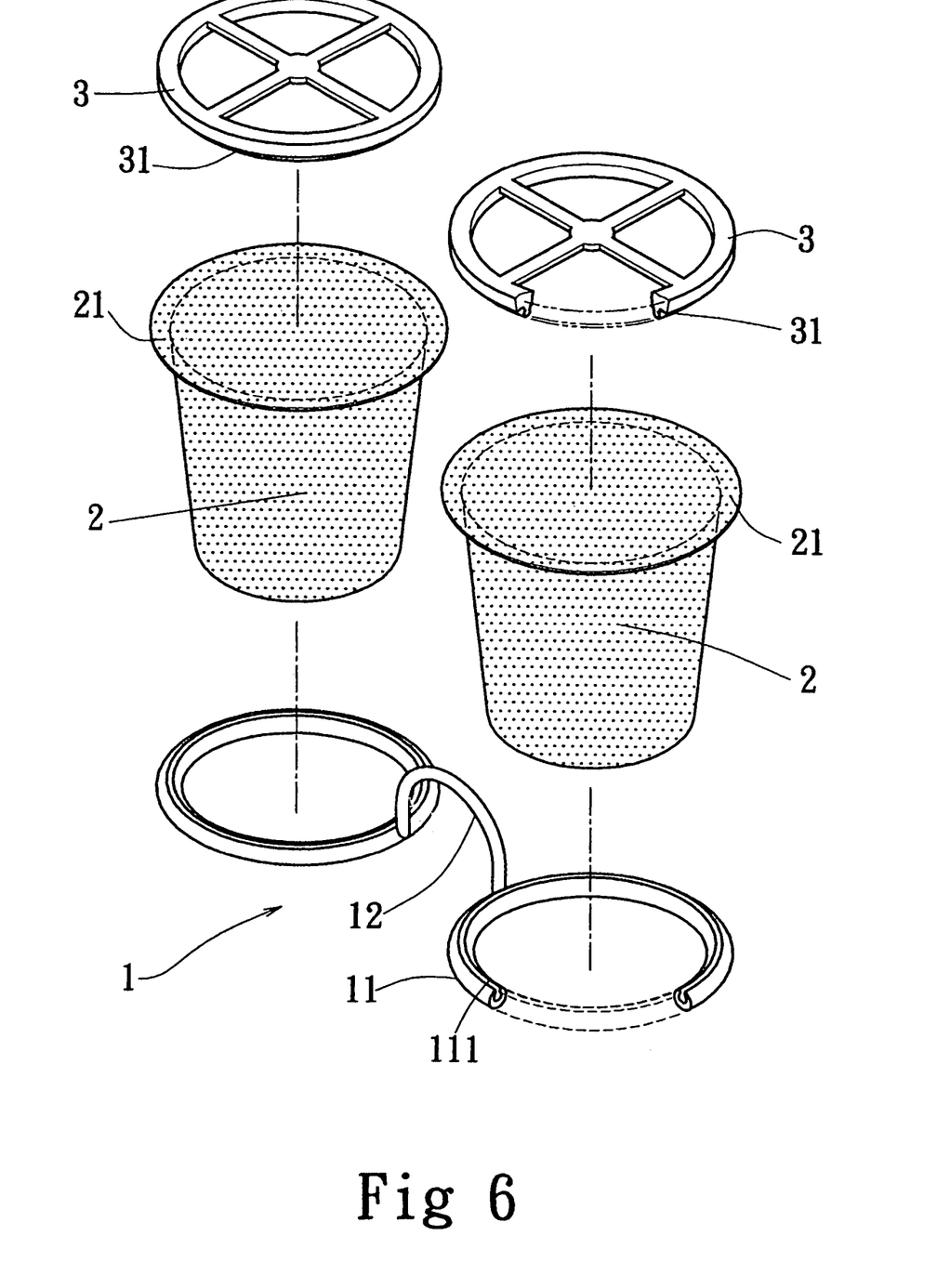
FIG. 6 is an exploded view to show yet another embodiment of the filtering assembly of the present invention.
Figure 7:
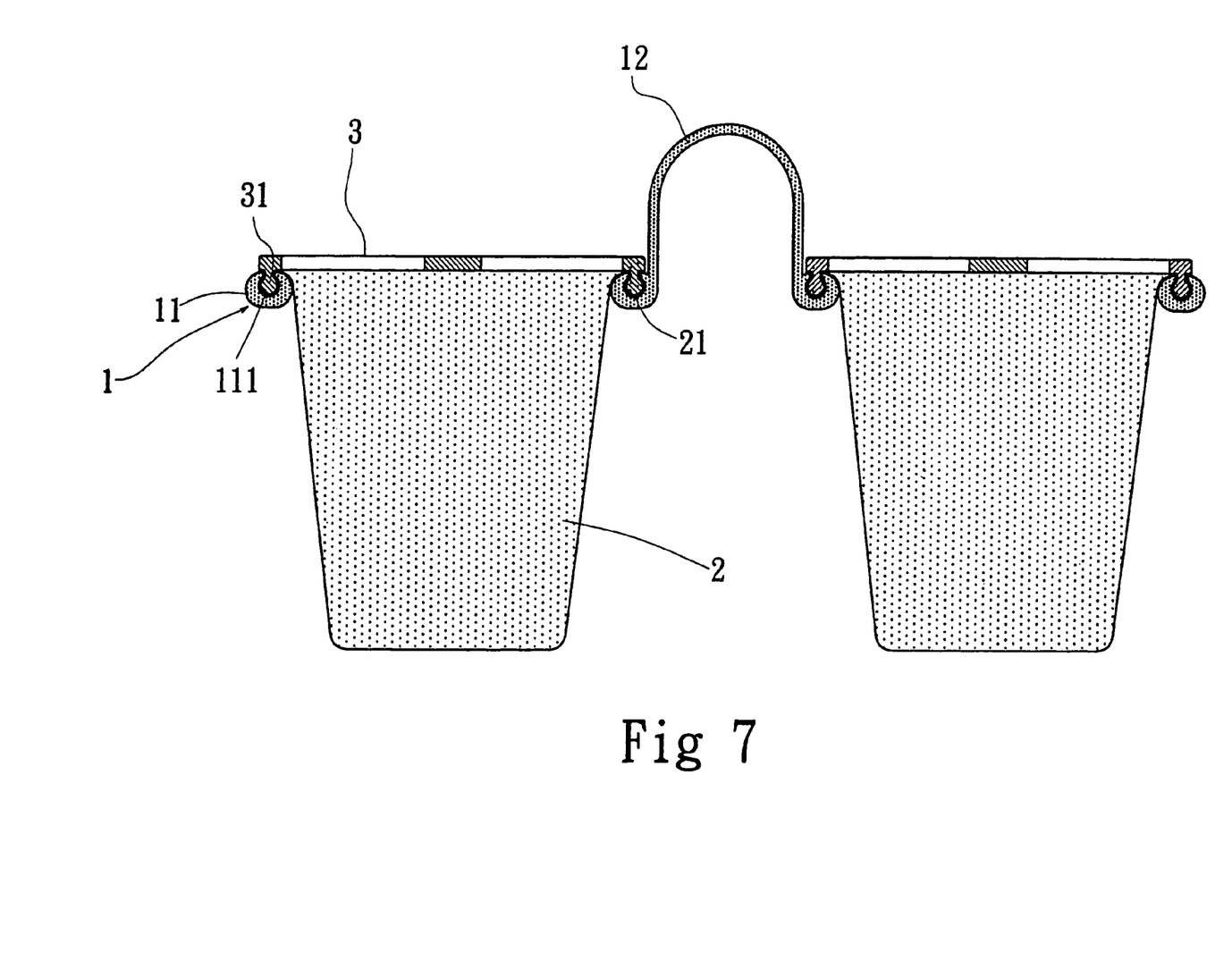
FIG. 7 is a cross sectional view of the filtering assembly of the present invention in FIG. 6.
Figure 8:
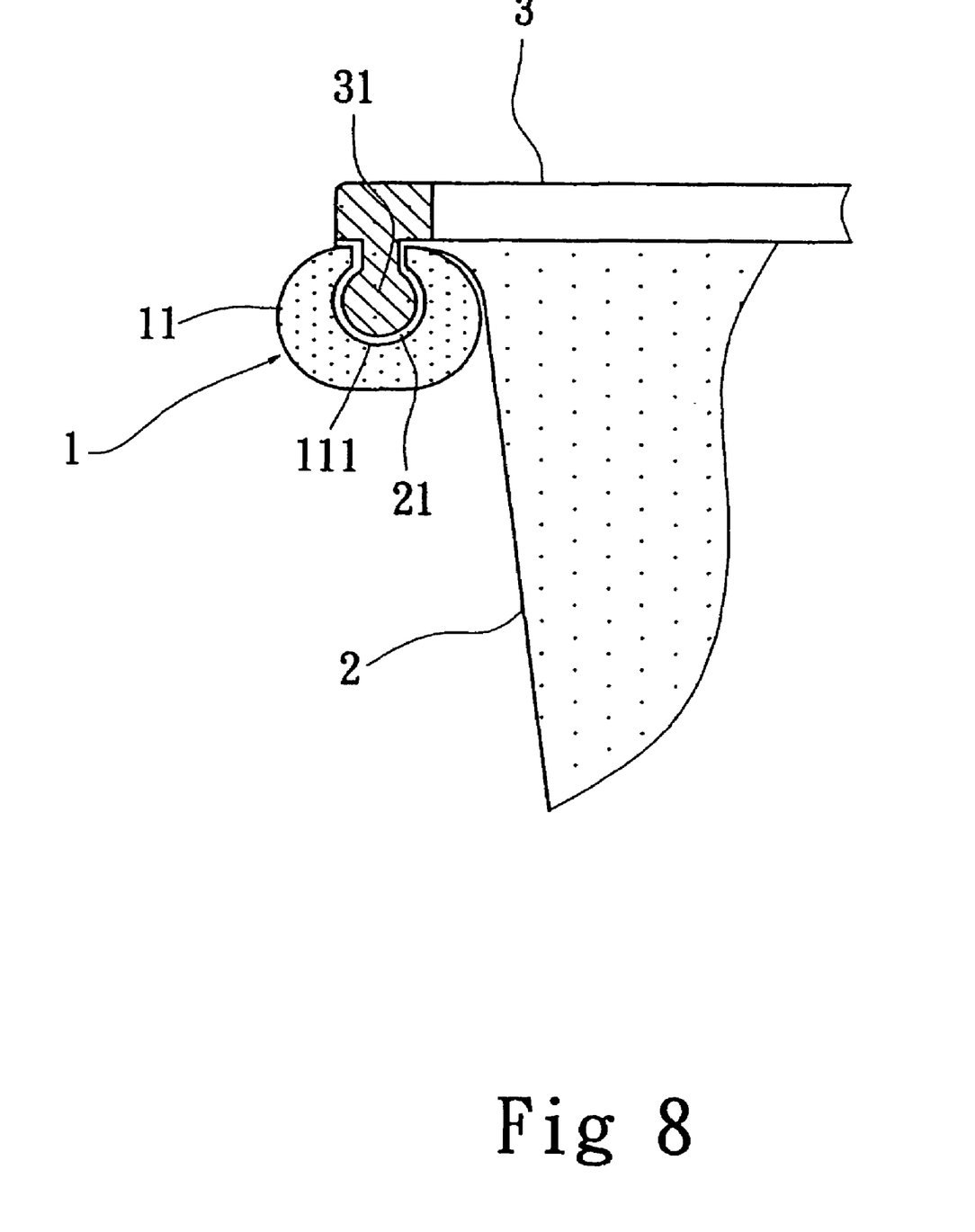
FIG. 8 is an enlarged cross sectional view of the connection of the insertion of a pressing member and the engaging slot of a ring in FIG. 6.

FIGS. 6 to 8 show another embodiment of the filtering assembly wherein each of the rings 11 includes an engaging slot 111 defined in a top surface thereof and each of the engaging slots 111 includes a narrow opening and a wide bottom. The two filtering members 2 each have a flange 21 extending outward from an end thereof. Two pressing members 3 are used to press the two flanges 21 into the engaging slots 111 of the two rings 11. Each pressing members 3 has an insertion 31 so that the insertions 31 press the flanges 21 into the engaging slots 111. The insertions 31 are shaped to be complementary to the engaging slots 111 and can be securely engaged with the engaging slots 111 to position the filtering members 2 to the rings 11. Each of the pressing members 3 is a collar and two bars crossly connected with each other are connected in each of the collars. By the two bars, the pressing members 3 press the top surfaces of the two filtering members 2 and this is helpful to position the filtering members 2 in stable status.

While we have shown and described the embodiment in accordance with the present invention, it should be clear to those skilled in the art that further embodiments may be made without departing from the scope of the present invention.

What is claimed is:

1. A filtering assembly in nasal cavities, comprising:
a connector having two rings connected by a link, and
two filtering members connected to the two rings, the two filtering members each having a flange extending outward from an end thereof and the flanges being secured to the rings, two pressing members pressing the two flanges, each of the rings including an engaging slot and each pressing member having an insertion, the insertions press the flanges into the engaging slots.

2. The assembly as claimed in claim 1, wherein the two filtering members are secured to the rings by way of heat fusion.

3. The assembly as claimed in claim 1, wherein each of the engaging slots includes a narrow opening and a wide bottom, the insertions are shaped to be complementary to the engaging slots.

4. The assembly as claimed in claim 1, wherein each of the pressing members is a collar and two bars crossly connected with each other are connected in each of the collars.

* * * * *